United States Patent [19]

Walker

[11] 4,118,582

[45] Oct. 3, 1978

[54] PURIFICATION OF SPENT ETHYLENE GLYCOL

[75] Inventor: Charles Carey Walker, Circleville, Ohio

[73] Assignee: E. I. Du Pont de Nemours and Company, Wilmington, Del.

[21] Appl. No.: 764,901

[22] Filed: Jan. 17, 1977

Related U.S. Application Data

[63] Continuation-in-part of Ser. No. 626,027, Oct. 28, 1975, abandoned.

[51] Int. Cl.$^2$ .................. C07C 69/76; C07C 29/24
[52] U.S. Cl. ........................................ 560/96; 560/79;
    568/871
[58] Field of Search ................ 260/647 R, 79; 560/96

[56] References Cited

U.S. PATENT DOCUMENTS

| | | | |
|---|---|---|---|
| 3,878,055 | 4/1975 | Cox et al. ...................... | 260/637 R |
| 4,013,519 | 3/1977 | Hoppert et al. ................ | 260/637 R |

FOREIGN PATENT DOCUMENTS

| | | | |
|---|---|---|---|
| 4,915,137 | 4/1974 | Japan ................................ | 260/637 R |
| 4,915,479 | 4/1974 | Japan ................................ | 260/637 R |
| 883,040 | 11/1961 | United Kingdom ............. | 260/637 R |

OTHER PUBLICATIONS

Jula, Inorganic Reductions with NaBH$_4$, Ventron Corp., Chem. Div., Congress St., Beverly, Mass. (1974).
Ventron Corp. Technical Bul. No. 47–A, Ventron Corp., Chem. Div., Beverly, Mass.
Anon., "Chem. Absts.", vol. 81, 21894(g) 1974, citing Fed. Regist. 28(173), 24342–24344 (1973).

*Primary Examiner*—James O. Thomas, Jr.
*Assistant Examiner*—G. T. Breitenstein

[57] ABSTRACT

Spent ethylene glycol recovered from polyester manufacture contains dissolved antimony catalyst residues and other impurities. Prior to distillation of the spent glycol to recover purified ethylene glycol, the antimony compounds are removed by adjusting the pH of the spent glycol to about 2 to 7, preferably 5 to 7, preferably by adding an organic acid (e.g., acetic acid) adding an alkali metal borohydride (e.g., sodium borohydride) in the absence of oxygen and with intimate mixing to form a metallic antimony precipitate, and recovering the precipitate. The process is further improved by adding a catalytic amount of a strong inorganic base, e.g., sodium hydroxide, prior to the pH adjustment step, to convert any terephthalyl values to dihydroxyethyl terephthalate which can be recovered.

12 Claims, 1 Drawing Figure

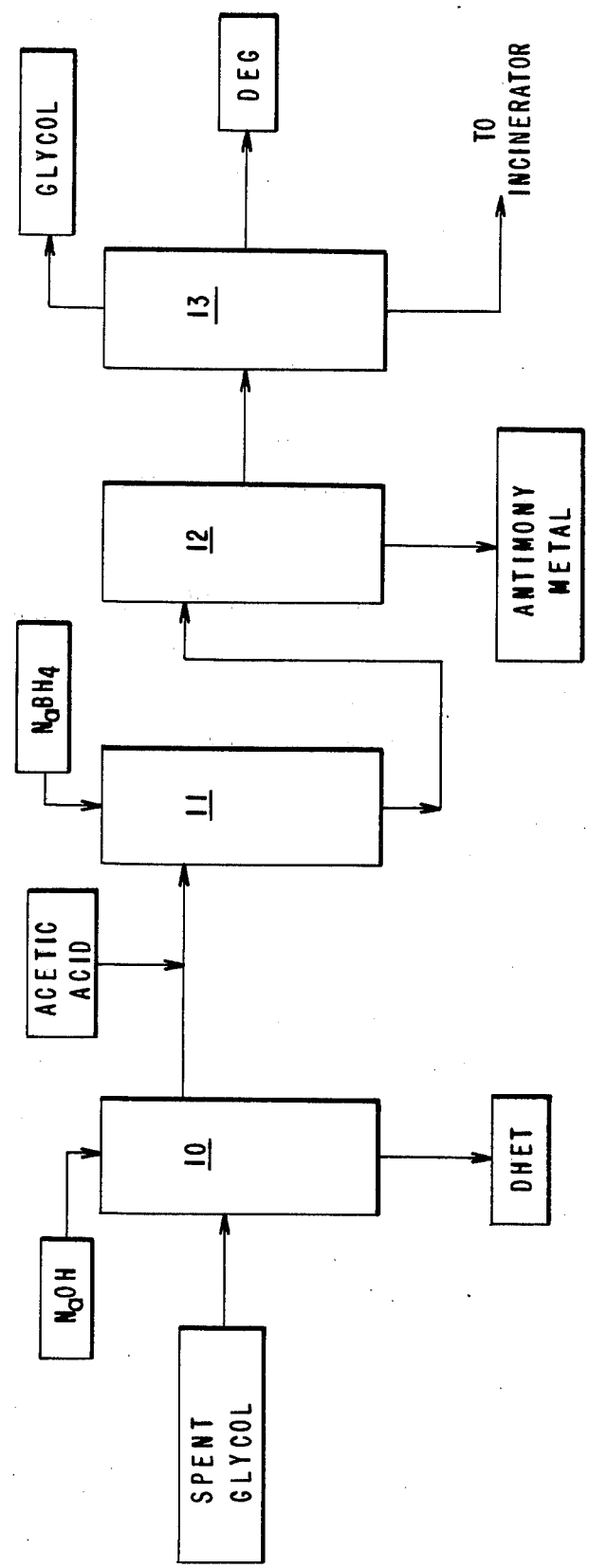

PURIFICATION OF SPENT ETHYLENE GLYCOL

CROSS-REFERENCE TO RELATED APPLICATION

This application is a continuation-in-part of U.S. patent application Ser. No. 626,027 filed Oct. 28, 1975, now abandoned.

BACKGROUND OF THE INVENTION

This invention relates to purification of ethylene glycol recovered during manufacture of linear polyesters such as poly(ethylene terephthalate), hereinafter "PET."

PET is a commercial film- and fiber-forming polyester which is generally manufactured by (1) esterifying terephthalic acid (TPA), or a lower alkyl ester of terephthalic acid such as dimethyl terephthalate (DMT), with ethylene glycol to form dihydroxyethyl terephthalate (DHET) and dimeric and higher esters thereof, and (2) polymerizing the DHET and esters thereof in the presence of an antimony oxide condensation catalyst to form PET while distilling off ethylene glycol liberated during the polymerization reaction. Thus, large quantities of ethylene glycol distillate, hereinafter "spent glycol," are produced during the polymerization reaction.

Unfortunately, the spent glycol contains impurities which will detract from product quality if it is simply recycled to the esterification step of the PET manufacturing process. For instance, a typical spent glycol contains minor quantities of diethylene glycol, water, aldehydes, and soluble antimony catalyst residues, such as various antimony compounds. Accordingly, it is standard practice in the industry to purify the spent glycol prior to recycle or diversion of the glycol to other uses, such as the manufacture of antifreeze.

The spent glycol is generally purified by a fractional distillation in which relatively pure ethylene glycol is recovered as the overhead stream. However, the glycol ordinarily obtained is only relatively pure and is not always suitable for recycle to form PET, except in the production of polymers where the contaminants do not adversely affect the properties of the ultimate product. When PET having little or no color is required, recovered spent glycol even after purification by fractional distillation is unsuitable for recycling in the process. The column bottoms, which contain concentrated quantities of the impurities, have been disposed of in various ways, including incineration, land burial, or ocean dumping. In a typical distillation, about 80 to 90% of the ethylene glycol present in the spent glycol is recovered in the overhead stream, the balance remaining in the column bottoms. More exhaustive distillation becomes uneconomical and leads to difficulty since it causes a greater buildup in the column bottoms of unrecoverable tars and residues.

Thus, substantial quantities of ethylene glycol, antimony, and terephthalyl values are lost during the conventional recovery of spent glycol. Terephthalyl values are TPA and esters and oligomers of TPA and glycols including diethylene glycol (DEG). Moreover, there are practical objections to the various proposals for disposal of the column bottoms. Expensive equipment is required to incinerate the large quantities of waste involved and to eliminate potential air pollutants, such as antimony compounds, from the incinerator stack. Disposal by land burial or ocean dumping may no longer be desirable because of environmental concerns.

Accordingly, there is a need for a process for the purification of spent glycol which improves the quality of the recovered glycol and which minimizes the problems of waste disposal mentioned hereinabove. Especially desired is an improved process wherein contaminants present in the spent glycol, such as antimony and terephthalyl values, can be economically recovered.

SUMMARY OF THE INVENTION

The present invention provides, in a process for the recovery of ethylene glycol from spent glycol formed in the manufacture of polyethylene terephthalate wherein terephthalic acid or a lower alkyl ester thereof and ethylene glycol are reacted to form dihydroxyethyl terephthalate, said dihydroxyethyl terephthalate is polymerized in the presence of an antimony oxide catalyst to form said polyethylene terephthalate and spent glycol containing antimony catalyst residues, and ethylene glycol is recovered by distillation from the spent glycol, the improvement comprising:

(a) adjusting the pH of the spent glycol to about 2 to 7;

(b) adding an alkali metal borohydride in an excess of about 20 to 200 mole percent to the spent glycol in the absence of oxygen at a temperature not greater than about 60° C. and with intimate mixing, to form a metallic antimony precipitate;

(c) separating the metallic antimony precipitate from the spent glycol in the absence of oxygen; and (d) distilling ethylene glycol from the spent glycol.

As used herein, the term "pH" means the apparent pH of the spent glycol as determined by wetting a strip of "pHydrion" test paper with distilled water, contacting the wet test paper with a drop of spent glycol, and comparing the resulting color of the test paper with a standardized pH/color chart.

The foregoing process can be further improved by adding a catalytic amount of a strong inorganic base, such as sodium hydroxide, to the spent glycol prior to step (a) to convert soluble terephthalyl values present therein to DHET which is insoluble in the spent glycol. The DHET is conveniently recovered by allowing it to settle in a holding tank or by filtration techniques.

BRIEF DESCRIPTION OF THE DRAWING

The FIGURE depicts a flow sheet of a specific embodiment of the process of this invention.

DESCRIPTION OF THE INVENTION

A typical spent glycol from a commercial PET manufacturing plant contains about 90 to 97% ethylene glycol, about 3 to 5% DEG, up to about 3% soluble terephthalyl values, minor quantities of water, generally less than about 1%, a minor quantity of aldehydes, such as acetaldehyde formed by the degradation of ethylene glycol, about 300 to 2500 ppm of antimony, in the form of dissolved organic antimony compounds, and trace quantities of other contaminants (percentages being by weight). Distillation procedures, such as fractional and flash distillation, are conventionally used to recover most of the ethylene glycol present in the spent glycol.

In accordance with the present invention, antimony compounds present in the spent glycol are reduced to metallic antimony, and thus precipitated, prior to distillation of ethylene glycol from the spent glycol or, if desired, after a portion of the ethylene glycol has been distilled from the spent glycol to reduce the volume of liquid handled during the antimony recovery process. An alkali metal borohydride is selected as the reducing agent since the residue borate salts are nontoxic, simplifying waste disposal. Sodium borohydride is preferred because of its general stability and its efficiency as a reducing agent in the glycol medium under the process conditions discussed hereinafter, and the invention is hereinafter described with sodium borohydride representing the alkali metal borohydride.

The spent glycol is basic in nature after DHET recovery. Thus, the sodium borohydride will not react at a reasonable rate, and therefore will not function as an effective reducing agent, unless the pH is adjusted to about 7 or below. This adjustment in pH is conveniently accomplished by the addition of an acid to the spent glycol from which the DHET has been recovered. Both organic and inorganic acids can be selected for this purpose although organic acids, such as acetic or formic acid, are preferred because of the buffering action their resultant salts provide.

The time required to complete the reduction is influenced by the degree to which the spent glycol pH is adjusted. As the pH is adjusted further below 7, reduction times tend to be shortened. Reaction efficiency is reduced at lower pH, however, since more of the sodium borohydride decomposes without reducing the dissolved antimony compounds; thus, larger borohydride excesses may be required to achieve an effective recovery of the antimony. Adjustment to a pH of about 5 to 7 is generally preferred for an efficient recovery of the antimony (i.e., recovery of 98% or more of the dissolved values) within a reasonable time, such as 48 hours or less, and with favorable reaction efficiency. In any event, the pH should not be adjusted to less than about 2 since toxic stibine gas may be generated under highly acidic conditions.

After the pH of the spent glycol has been adjusted, sodium borohydride is added under controlled conditions which results in an efficient yield of antimony. The sodium borohydride can be added either in solid form or as a solution in water or an organic medium, such as ethylene glycol. The reduction proceeds satisfactorily at room temperature (i.e., 25° to 30° C.) and there is no need to heat the spent glycol. The spent glycol should not be hotter than about 60° C. since sodium borohydride will rapidly decompose at higher temperatures. Since the alkali metal borohydride is basic, the pH of the reaction solution rises steadily as it is added. Depending upon the starting pH of the glycol after pH adjustment, the pH near the end of the reaction may rise above 7. This, however, does not adversely affect the reduction reaction.

Intimate mixing of the spent glycol and sodium borohydride is important, both as they are brought together and during the course of the reduction. Sodium borohydride begins to decompose when it initially contacts the spent glycol and, unless there is intimate mixing of the components, reaction efficiency suffers. For that reason, the spent glycol is continuously agitated during the course of the reduction.

Oxygen is excluded from the spent glycol during the process, at least until the reduced antimony has been recovered, since oxygen will rapidly re-oxidize the antimony. In the presence of oxygen, the finely divided antimony precipitate rapidly redissolves, and it is believed that oxygen reacts with the precipitate and the glycol medium to form glycol-soluble organic antimony compounds, which, being in solution, are not in a state conducive to easy removal. Accordingly, the reduction of antimony and its removal, as by filtration, are accomplished in a completely filled reactor, or under an inert atmosphere such as nitrogen, to avoid entrapment of atmospheric oxygen as the spent glycol is agitated. Otherwise, antimony recovery and reaction efficiencies will be diminished.

The chemical equation for the reduction of trivalent antimony with borohydride is:

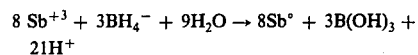

Thus, 3 moles of borohydride will reduce 8 moles of antimony, or, stating the same thing differently, reduction of one mole of antimony requires three-eighths (0.375) mole of borohydride. Under the prescribed conditions, up to about 98% or more of the dissolved antimony compounds can be precipitated as metallic antimony when using a 20 to 200% mole excess of sodium borohydride. Accordingly, a 20% mole excess of borohydride is 0.45 mole of borohydride per mole of antimony, and a 200% mole excess of borohydride is 1.125 mole of borohydride per mole of antimony. The time required to accomplish the reduction will be shorter as the pH approaches 5, or as the excess of sodium borohydride approaches 200%, and will typically be in the range of about 1 to 24 hours. Since favorable reduction efficiencies can be achieved in reasonable times under these conditions, it is generally not economically warranted to employ a sodium borohydride excess greater than about 200%, although larger quantities can be employed if desired.

The reduced antimony precipitates from the spent glycol as a black sludge which is recovered by decanting the spent glycol or by filtration. If filtration is employed, the filter medium should be suitably sized to capture colloidal-sized particles, i.e., the filter openings should be smaller than 1 micron.

The recovered antimony can be oxidized, in a furnace, for instance, to convert it to antimony oxide. The reclaimed antimony oxide may be recycled to the PET plant for reuse as a polymerization catalyst. Also, the precipitated antimony, after washing, may be suspended in glycol and by means of agitation with air be converted to a catalytically active solution.

The soluble terephthalyl values present in the spent glycol tend to be glycolyzed, under slightly basic conditions, to form insoluble DHET which is readily recovered by decanting or filtering the spent glycol. Thus, it may be desirable, optionally, to treat spent glycol with a catalytic quantity of a strong inorganic base prior to step (a) of the process as hereinbefore described. By "catalytic quantity of a strong inorganic base" is meant a quantity of the base, such as sodium hydroxide or other alkali metal hydroxide, sufficient to catalyze the glycolysis but insufficient to form soluble metallic terephthalate salts. A typical concentration is about 0.03 to 0.06 moles of the inorganic base per liter of spent glycol. Under these conditions, about 40 to 60% of the terephthalyl values present in the spent glycol can typically be recovered as DHET, which can be reused in the PET plant.

After treatment of the spent glycol to recover antimony, the glycol is distilled in conventional manner to form an overhead ethylene glycol stream having sufficient purity to be recycled for the manufacture of PET, a side-stream of diethylene glycol which is incinerated or recovered, and a still bottoms which contains the remaining impurities. It has been found that ethylene glycol can be recovered in the overhead stream exhibiting a purity (as determined by ultraviolet scan) substantially purer than the overhead glycol conventionally obtained from the fractional distillation of spent glycol without the removal of antimony compounds according to this invention. Purified ethylene glycol has been obtained using the improved process of this invention having a purity about the same as that of virgin ethylene glycol. More specifically, ethylene glycol to be used in making high quality PET should have an ultraviolet transmission at 3500 angstrom units of at least 98%; ethylene glycol distilled from spent glycol has an ultraviolet transmission of only about 81% at 3500 angstroms, whereas following removal of antimony by the present invention the distilled ethylene glycol has an ultraviolet transmission of at least about 98% at 3500 angstroms. The present invention also improves ultraviolet transmission at other wavelengths. (Ultraviolet transmission is the percent transmission of light through a sample of the material 1-centimeter thick.) The still bottoms, containing residual antimony and terephthalyl values, can be incinerated or a major portion thereof can be mixed with incoming spent glycol for further recovery.

A specific embodiment of the process as depicted in the drawing may be performed as follows (wherein parts and percentages are by weight except as noted):

One hundred parts of spent glycol taken from a PET plant containing about 2400 ppm of dissolved antimony are mixed in reactor 10 at room temperature with a catalytic amount of NaOH, e.g., 0.3 ml. of a 46% aqueous NaOH solution per 100 ml. of spent glycol. After about 16 hours, the DHET formed as a solid precipitate is separated by decanting the supernatant glycol. The latter is then adjusted to a pH (as measured hereinabove) of about 5 by the addition of acetic acid. Under an inert atmosphere of nitrogen, the spent glycol is vigorously mixed in the reduction reactor 11 with $NaBH_4$ by the addition of an aqueous solution containing about 12% $NaBH_4$, 42% NaOH, the balance being water ("Sodium Borohydride-SWS," commercially available from Ventron Corp., Beverly, Mass.). The amount of $NaBH_4$ solution should be in a ratio of 0.33 ml. of solution per 100 ml. of spent glycol.

The antimony compounds in the spent glycol are converted into antimony metal. The reaction mixture is pumped into a filter 12 where the antimony metal is removed. About 98.5% of the antimony originally present in the spent glycol can be recovered, leaving, for example, about 33 ppm antimony in the glycol.

The glycol stream is then sent to a fractionating column 13 operated under reduced pressure (e.g., 100 mm. Hg) where the purified ethylene glycol is taken off as overhead stream, DEG comes off as a side stream, and the column bottoms are removed and sent to an incinerator. The recovered glycol is of polymer-grade quality.

As previously indicated, the column bottoms may be recycled for further recovery.

I claim:

1. In a process for the recovery of ethylene glycol from spent glycol formed in the manufacture of polyethylene terephthalate wherein terephthalic acid or a lower alkyl ester thereof and ethylene glycol are reacted to form dihydroxyethyl terephthalate, said dihydroxyethyl terephthalate is polymerized in the presence of an antimony oxide catalyst to form said polyethylene terephthalate and spent glycol containing antimony catalyst residues, and ethylene glycol is recovered by distillation from the spent glycol, the improvement comprising:
   (a) adjusting the pH of the spent glycol to about 2 to 7;
   (b) adding an alkali metal borohydride in an excess of about 20 to 200 mole percent to the spent glycol in the absence of oxygen at a temperature not greater than about 60° C. and with intimate mixing, to form a metallic antimony precipitate;
   (c) separating the metallic antimony precipitate from the spent glycol in the absence of oxygen; and
   (d) distilling ethylene glycol from the spent glycol.

2. The process of claim 1 wherein the distilled ethylene glycol recovered has an ultraviolet transmission at 3500 angstrom units of at least about 98%.

3. The process of claim 1 wherein the distilled ethylene glycol recovered is recycled to the manufacturing process.

4. The process of claim 1 wherein the pH is adjusted in step (a) by adding an organic acid to the spent glycol.

5. The process of claim 4 wherein the organic acid is acetic acid.

6. The process of claim 4 wherein the pH is adjusted to about 5 to 7.

7. The process of claim 1 wherein, in step (b), sodium borohydride is added to spent glycol maintained under an atmosphere or an inert gas and having a pH of about 5 to 7.

8. The process of claim 1 wherein said spent glycol contains terephthalyl values, said process further comprising, prior to pH adjustment of step (a), adding a catalytic quantity of a strong inorganic base to catalyze the glycolysis of said terephthalyl values to form a precipitate of dihydroxyethyl terephthalate, and recovering said dihydroxyethyl terephthalate.

9. The process of claim 8 wherein the inorganic base is sodium hydroxide.

10. The process of claim 9 wherein the inorganic base is added in the quantity of 0.03 to 0.06 mole per liter of spent glycol.

11. The process of claim 1 wherein the metallic antimony precipitate obtained in step (c) is oxidized and recycled as catalyst in the manufacturing process.

12. The process of claim 8 wherein the metallic antimony precipitate obtained in step (c) is oxidized and recycled as catalyst in the manufacturing process.

* * * * *